(12) United States Patent
Moake

(10) Patent No.: US 8,583,377 B2
(45) Date of Patent: Nov. 12, 2013

(54) METHODS AND SYSTEMS OF FORMATION DENSITY MEASUREMENTS IN THE PRESENCE OF INVASION OF DRILLING FLUIDS

(75) Inventor: Gordon L. Moake, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 176 days.

(21) Appl. No.: 13/282,270

(22) Filed: Oct. 26, 2011

(65) Prior Publication Data

US 2013/0110404 A1 May 2, 2013

(51) Int. Cl.
  *G01V 1/40* (2006.01)
(52) U.S. Cl.
  USPC ............................................................ 702/8
(58) Field of Classification Search
  CPC ....................................................... G01V 1/40
  USPC ............................................. 702/8, 182–185
  See application file for complete search history.

(56) References Cited

U.S. PATENT DOCUMENTS

| | | | |
|---|---|---|---|
| 4,035,640 A | 7/1977 | Arnold et al. | |
| 4,698,501 A | 10/1987 | Paske | |
| 4,879,463 A | 11/1989 | Wraight et al. | |
| 7,282,704 B2 | 10/2007 | Guo | |
| 2007/0040110 A1 | 2/2007 | Ellis et al. | |
| 2010/0292927 A1 | 11/2010 | Jacobson et al. | |
| 2011/0137566 A1* | 6/2011 | Jacobson et al. | 702/8 |
| 2011/0168879 A1 | 7/2011 | Evans et al. | |

OTHER PUBLICATIONS

Search Report and Written Opinion issued Jan. 29, 2013 in International Application No. PCT/US2012/051525.
Per Cator Berg, et al., "Drilling, Completion, and Openhole Formation Evaluation of High-Angle Wells in High-Density Cesium Formate Brine: The Kvitebjorn Experience, 2004-2006", Feb. 22-22, 2007, SPE/IDAC Paper No. 105733.
Gordon L. Moake, "Using Computer Modeling to Generate Accurate PE Equations", May 14-18, 2011, SPWLA 52nd Annual Logging Symposium.

* cited by examiner

*Primary Examiner* — Edward Raymond
(74) *Attorney, Agent, or Firm* — Mark E. Scott; Conley Rose, P.C.

(57) ABSTRACT

Formation density measurements in the presence of invasion of drilling fluids. At least some of the illustrative embodiments are methods including: irradiating a formation with gammas from a source of gammas, wherein drilling fluid has invaded the formation, and wherein Pe of the drilling fluid that has invaded the formation is greater than Pe of the formation; determining a first value indicative of a parameter of the formation; determining a second value indicative of a parameter of the formation; determining a third value, the third value determined based on gammas in an energy range different than used in determining the first value; and calculating, using the first, second, and third values, information such as a standoff, a formation porosity, a formation density prior to invasion by the drilling fluid, and radial depth of invasion of the drilling fluid into the formation.

20 Claims, 11 Drawing Sheets

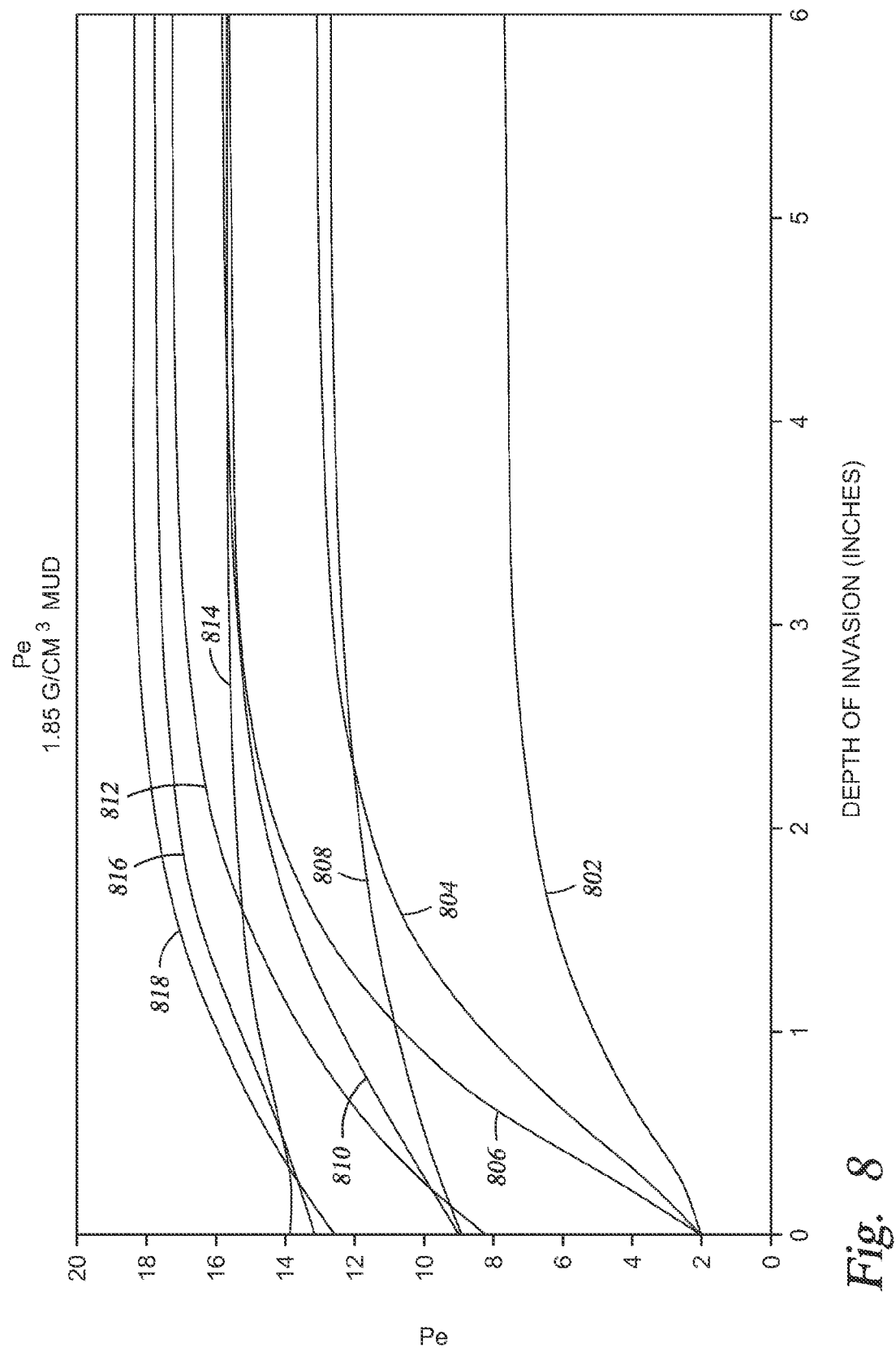

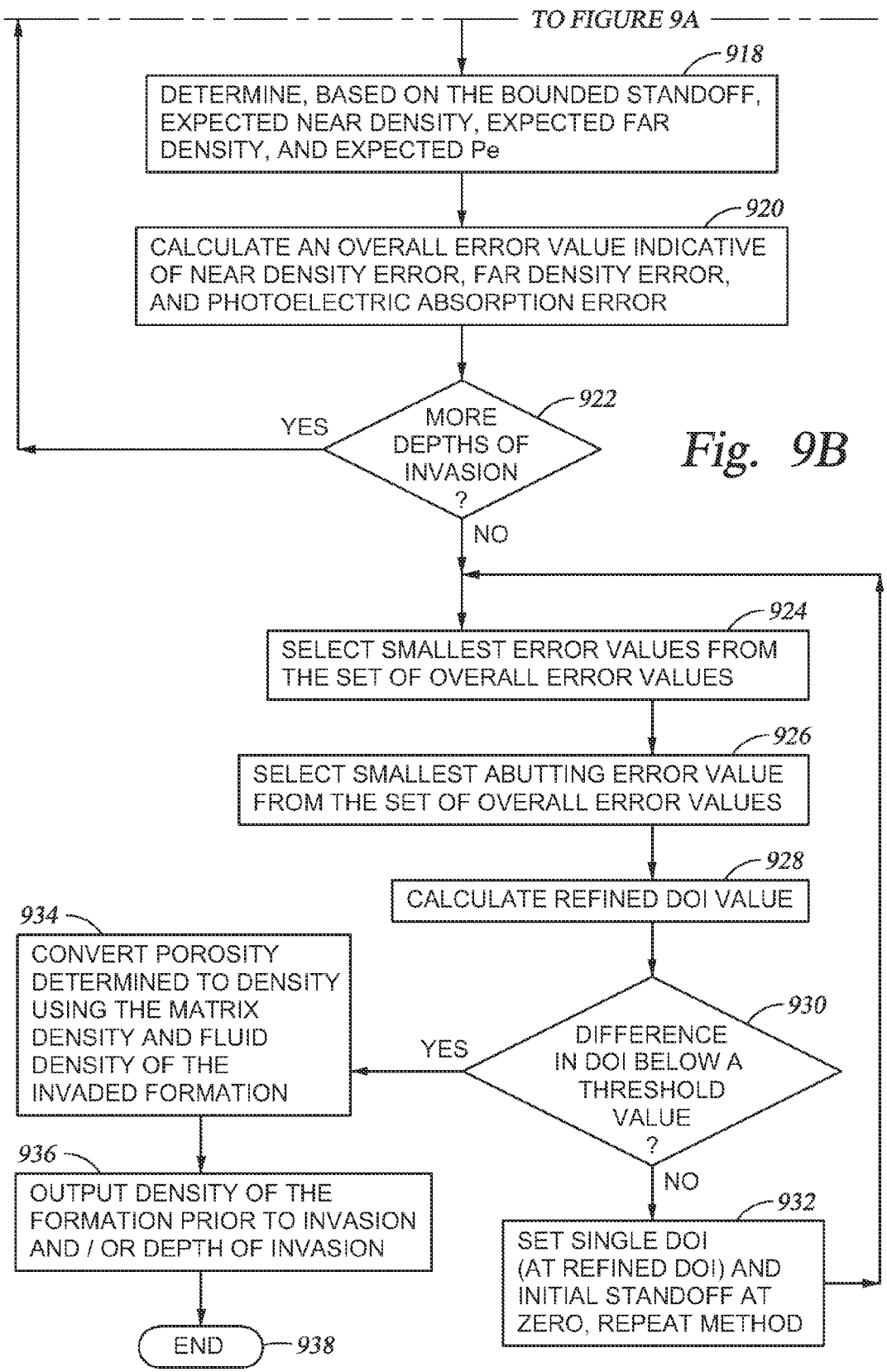

METHODS AND SYSTEMS OF FORMATION DENSITY MEASUREMENTS IN THE PRESENCE OF INVASION OF DRILLING FLUIDS

CROSS-REFERENCE TO RELATED APPLICATIONS

None.

BACKGROUND

In drilling operations a drilling fluid is used, and the drilling fluid has many purposes. For example, drilling fluid may cool and lubricate the drill bit during drilling. The drilling fluid may carry cuttings created downhole back to the surface for disposal. Moreover, the drilling fluid may provide a hydrostatic balance of pressures downhole. That is, the hydrocarbons in a formation have or are under a certain amount of pressure, and the weight of the column of drilling fluid within the borehole provides a counter balancing pressure which prevents the hydrocarbons from escaping to the surface in an uncontrolled manner.

A perfect hydrostatic balance is difficult to achieve, and thus to avoid failure in many cases the density of the drilling fluid is controlled such that the hydrostatic pressure of the drilling fluid downhole is greater than the pressure of the hydrocarbons in the formation. Because of the pressure difference, the drilling fluid may be forced into the formation (i.e., invade the formation). For water-based and oil-based drilling fluids, the invasion does not present significant issues with respect to measuring formation properties (such as density or porosity) because the drilling fluid that actually enters the formation has similar characteristics (e.g., density, photoelectric attenuation coefficient) to the displaced hydrocarbons, and the invasion is to some extent self limiting. However, a new family of drilling fluids is being used in the industry, the new family of drilling fluid comprising "formates" (e.g., cesium formate). Invasion of formates into a formation adversely affect the ability of logging tools to measure formation properties (again, such as density or porosity).

BRIEF DESCRIPTION OF THE DRAWINGS

For a detailed description of exemplary embodiments, reference will now be made, by way of example only, to the accompanying drawings in which:

FIG. 8 shows a plot of modeled Pe in accordance with at least some embodiments;

NOTATION AND NOMENCLATURE

Figure 1:
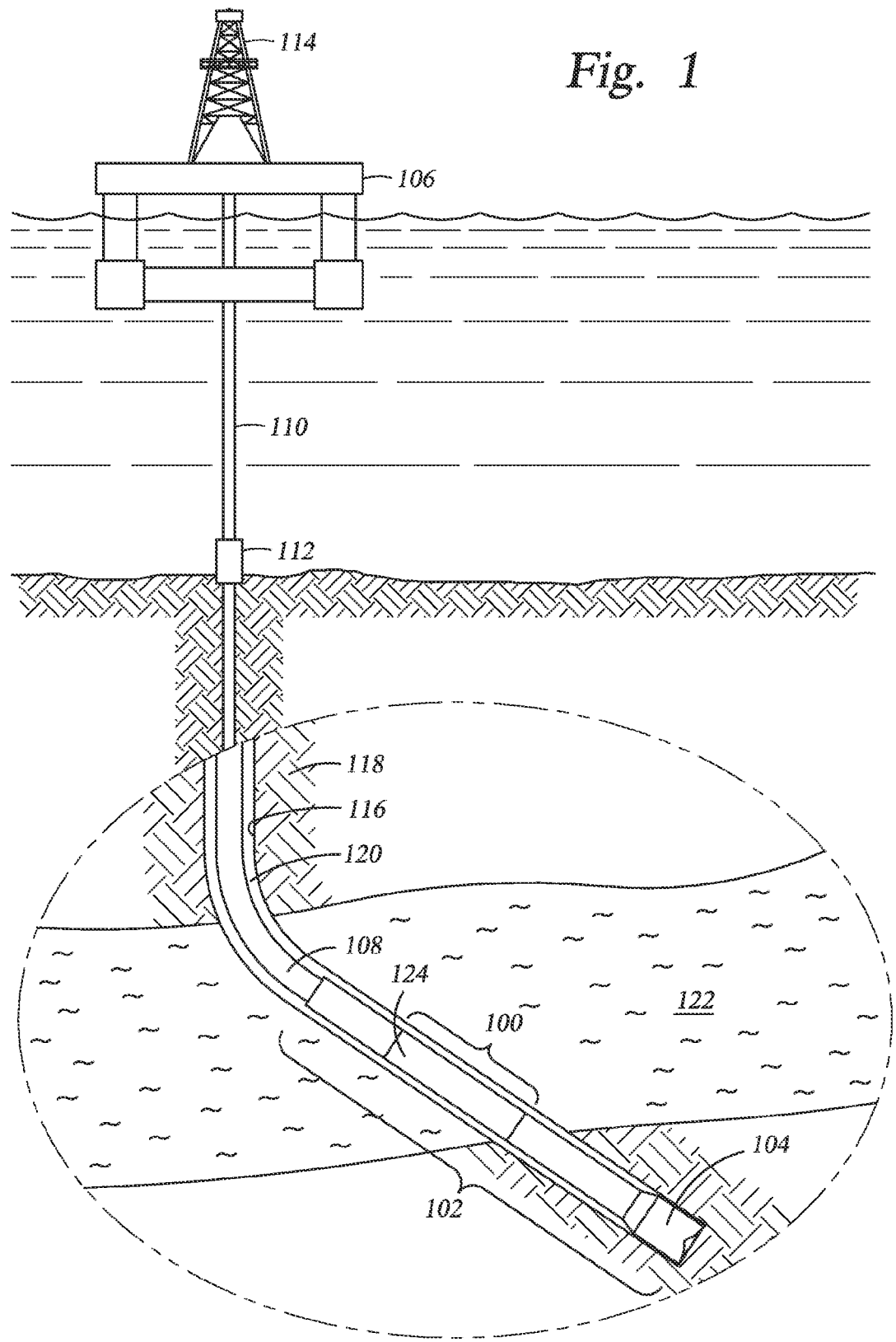
FIG. 1 shows a subsea system in accordance with at least some embodiments.

Certain terms are used throughout the following description and claims to refer to particular system components. As one skilled in the art will appreciate, oilfield service companies may refer to a component by different names. This document does not intend to distinguish between components that differ in name but not function.

In the following discussion and in the claims, the terms "including" and "comprising" are used in an inclusive fashion, and thus should be interpreted to mean "including, but not limited to . . . ". Also, the term "couple" or "couples" is intended to mean either an indirect or direct connection. Thus, if a first device couples to a second device, that connection may be through a direct connection or through an indirect connection via other devices and connections.

"Gamma" or "gammas" shall mean electromagnetic radiation emitted from nuclear decay of particles or the annihilation of particles, and shall include such radiation whether such radiation is considered a particle (i.e., gamma particle) or a wave (i.e., gamma ray or wave).

"Different", with respect to ranges of gamma energy, shall mean that the ranges have one or both of a different lower boundary energy or a different upper boundary energy, but shall not be read to require that the two energy ranges are mutually exclusive.

Labeling claim limitations with designators (e.g., a), b), c), and the like) shall not be read to require that the limitations be performed in any particular order.

"Pe" shall mean a value proportional to the ratio of photoelectric absorption cross-section of a substance (e.g., drilling fluid, earth formation) to the Compton cross-section for that substance.

Pe of a drilling fluid that has invaded a formation shall refer to at least a portion of the drilling fluid in at least a portion of the formation, and shall refer to the drilling fluid at a distance within the formation where particulates in the drilling fluid have be removed by the drilling fluid flowing into the formation.

"About", with respect to energy of gammas, shall mean within ten (10) percent of the stated energy. "About" with respect to distance measures shall mean within ten (10) percent of the stated distance. "About" with respect to Pe shall mean within ten (10) percent of the recited Pe.

"Irradiating" with respect to gammas and a formation shall mean exposing the formation to gammas, and shall not refer in any sense to how such gammas are created.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

The various embodiments are directed to methods and related systems of measuring formation properties when the formation has been invaded by a drilling fluid comprising formates (e.g., cesium formate, potassium formate, or the like). Before turning to specific issues associated with formates invading a formation, the specification first turns to illustrative systems to orient the reader to the systems within which the various embodiments may be practiced.

FIG. 1 shows a bottomhole assembly 102 for a subsea drilling operation, where the bottomhole assembly 102 comprises a formation evaluation tool 100 and a drill bit 104. The bottomhole assembly 102 is lowered from a drilling platform 106 by way of a drill string 108. The drill string 108 extends through a riser 110 and a well head 112. Drilling equipment supported within and around derrick 114 rotates the drill string 108 and the drill bit 104, causing the bit 104 to form a borehole 116 through the formation material 118. The volume defined between the drill string 108 and the borehole 116 is referred to as the annulus 120. The borehole 116 penetrates subterranean zones or reservoirs, such as reservoir 122, believed to contain hydrocarbons in a commercially viable quantity. In addition to the formation evaluation tool 100, the bottomhole assembly 102 may also contain various other systems, such as a down hole drill motor, a rotary steerable tool, a mud pulse telemetry system, and other measuring-while-drilling and/or logging-while-drilling sensors and systems.

Figure 2:
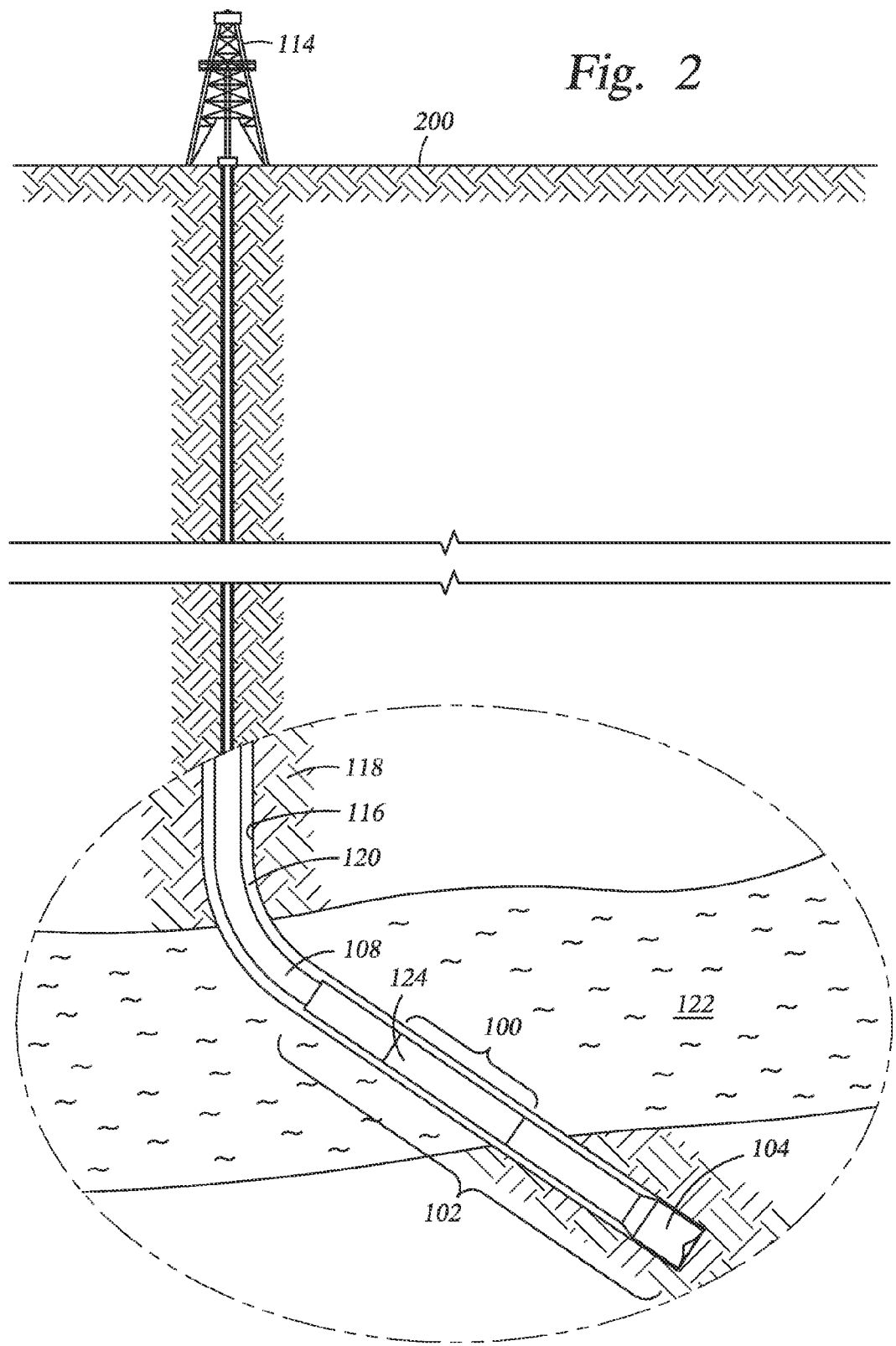
FIG. 2 shows a land-based system in accordance with at least some embodiments.

FIG. 2 shows bottomhole assembly 102 in use in a land-based drilling operation. In particular, the bottomhole assembly 102 again comprises formation evaluation tool 100 and drill bit 104. The bottomhole assembly 102 is lowered from the surface 200 by equipment associated with derrick 114. Drilling equipment supported within and around derrick 114 rotates the drill string 108 and the drill bit 104, causing the bit 104 to form a borehole 116 through the formation material 118.

Referring simultaneously to FIGS. 1 and 2, in some embodiments the information gathered by the formation evaluation tool 100 may be stored within the tool 100 and read when the formation evaluation tool 100 is raised to the platform 106 or raised to the surface 200. In other embodiments, some or all the information gathered by the tool may be sent to the platform 106 or surface 200 while the formation evaluation tool 100 is within the borehole 116. For example, some or all the information gathered by the formation evaluation tool 100 may be sent encoded in pressure pulses in the drilling fluid within the drill string 108. In yet still other embodiments, the information gathered by the formation evaluation tool 100 may be sent over a communication pathway embedded within the pipes of the drill string 108, such as by electrical conductors or optical conductors.

The formation evaluation tool 100 may be coupled within the bottomhole assembly 102 by any suitable mechanism. For example, in some embodiments the formation evaluation tool 100 has a threaded male "pin" end connector on one end, and a threaded female "box" end connector on the other end, such that the formation evaluation tool 100 couples to other components of the bottomhole assembly 102. In some cases, at least a portion of the outer surface 124 of the tool body forms a pressure vessel within which various components for generating gammas and detecting gammas are located. Moreover, a fluid conduit (not visible in FIG. 1) may also reside within the outer surface 124, and drilling fluid passes through the fluid conduit on its journey to the drill bit 104.

Figure 3:
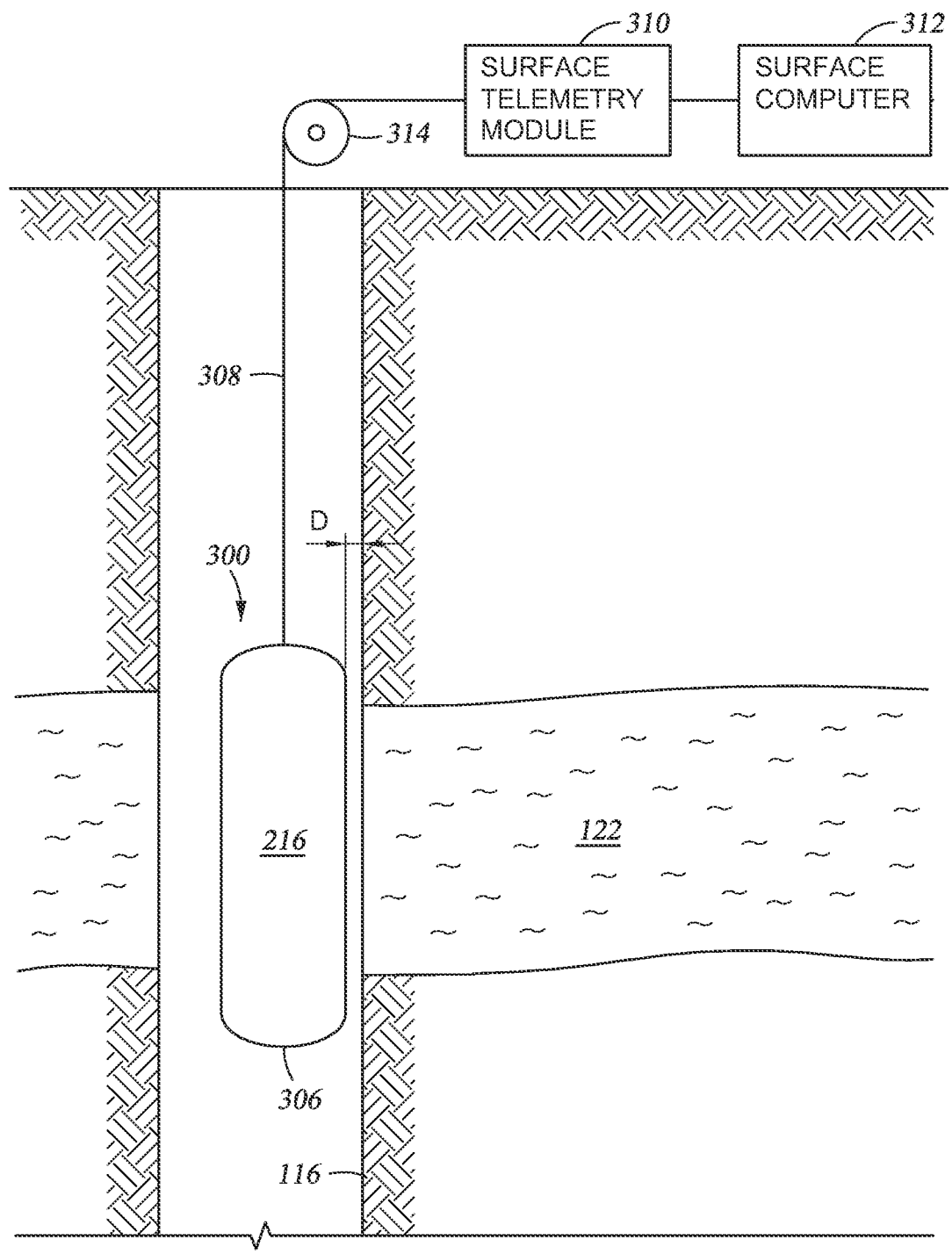
FIG. 3 shows a wire-line system in accordance with at least some embodiments.

While in some embodiments the formation evaluation tool is used in drilling operations, in yet still other embodiments the formation evaluation tool is used in wireline operations. In particular, FIG. 3 illustrates a wireline logging system that comprises a formation evaluation tool 300 placed within a borehole 116 proximate to a formation 122 of interest. The formation evaluation tool 300 comprises a tool body in the form of a pressure vessel 306 within which various subsystems of the formation evaluation tool 300 reside, and in the illustrative case of FIG. 3 the pressure vessel 306 is suspended within the borehole 116 by a cable 308. Cable 308, in some embodiments a multi-conductor armored cable, not only provides support for the pressure vessel 306, but also in these embodiments communicatively couples the formation evaluation tool 300 to a surface telemetry module 310 and a surface computer 312. The formation evaluation tool 300 may be raised and lowered within the borehole 116 by way of the cable 308, and the depth of the tool 300 within the borehole 116 may be determined by depth measurement system 314 (illustrated as a depth wheel). FIG. 3 is also illustrative of permanent or semi-permanent installations (e.g., installations within monitoring boreholes).

Regardless of the type of tool, in many cases the formation evaluation tool will be offset from the wall of the borehole 116. For example, in FIG. 3 pressure vessel 306 is shown to reside at a certain distance D from the wall of the borehole 116. The distance that the formation evaluation tool resides from the wall of the borehole 116 is referred to as standoff. While in FIG. 2 the standoff distance D is shown to be uniform along the length of the formation evaluation tool, in other cases the standoff distance may be different as a function of longitudinal distance along the tool. While possible to include devices to reduce the standoff, for formation evaluation tools such as shown in FIGS. 1 and 2, standoff will almost always be present. The standoff of the tool affects the measurement of formation parameters.

Figure 4:
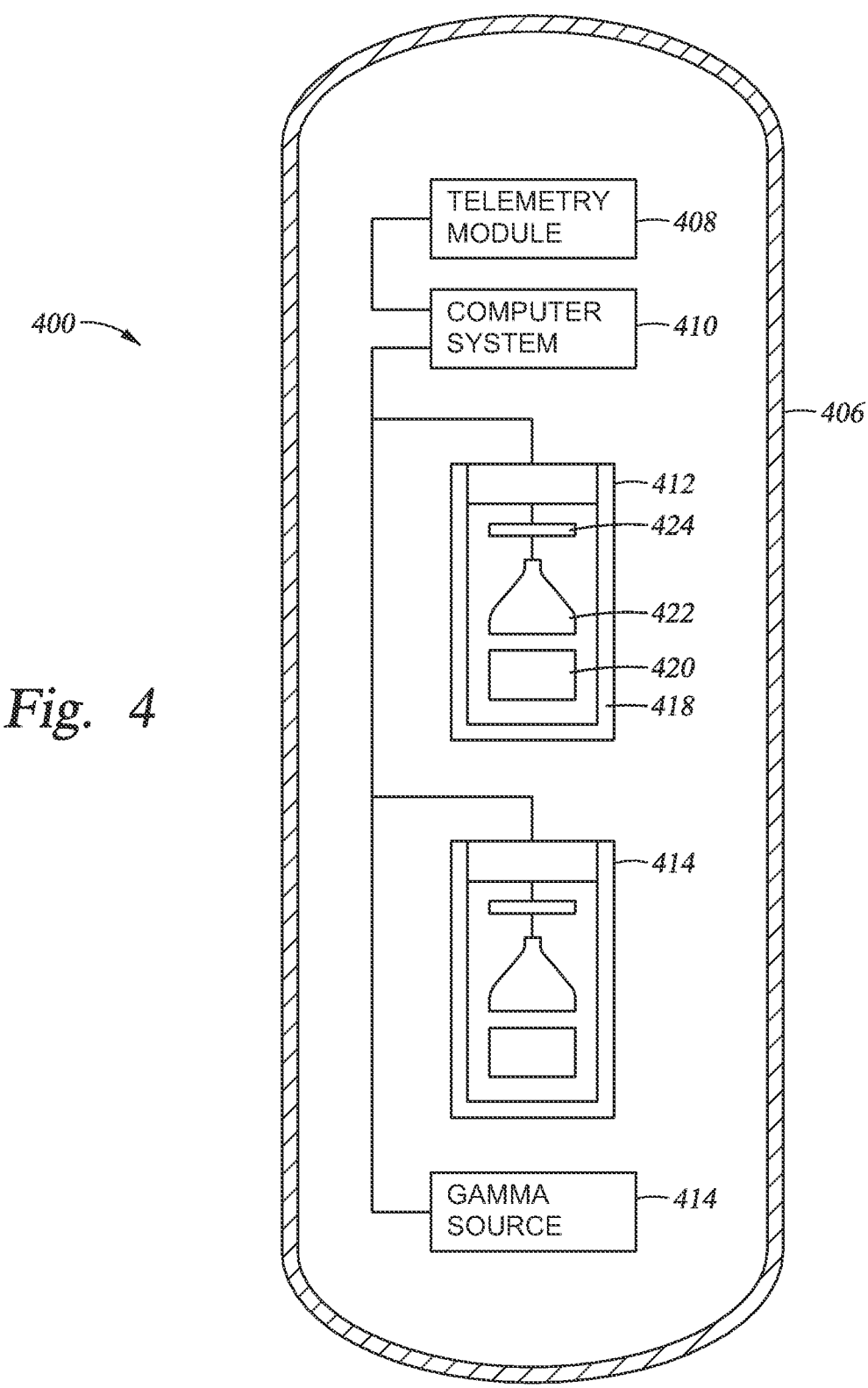
FIG. 4 shows a simplified cross-sectional view of a tool in accordance with at least some embodiments.

FIG. 4 shows a simplified partial cross-sectional view of a formation evaluation tool 400 in accordance with at least some embodiments. Formation evaluation tool 400 is illustrative of formation evaluation tool 100 in bottomhole assembly 102, wire-line formation evaluation tool 300, or permanent or semi-permanent logging installations. A tool body in the form of a pressure vessel 406 seals the various internal components from contact with borehole fluids and pressures. Within the pressure vessel 406 illustratively resides a telemetry module 408, computer system 410, a first or far gamma detector 412 (named based on relative distance from the gamma source), a second or near gamma detector 414 (named based on relative distance from the gamma source), and a gamma source 416. Gamma detectors 412 and 414 detect the arrival and energy of gammas, and in FIG. 4 the gamma detectors 412 and 414 are shown above the gamma source 416. In other embodiments, the gamma detectors 412 and 414 may be below the gamma source 416. In a particular embodiment, the far gamma detector 412 is a longitudinal distance (i.e., measured along the long axis of the tool 400) of about 14 inches from the gamma source 416, and the near gamma detector 414 is a longitudinal distance of about 6 inches from the gamma source 416, but other spacing, and additional gamma detectors, may be equivalently used.

Gamma source 416 is a continuous or controllable source of gammas. In a particular embodiment, gamma source 416 produces gammas having energies of above 600 kilo-electron Volt (keV), and in some cases the gamma source 416 produces gammas having energy of about 663 keV. Gamma source 416 is shown electrically coupled to the computer system 410 in FIG. 4 for controllable (i.e., pulsed) gamma sources (e.g., electron accelerator). In the case of pulsed gamma sources, the gamma source 416 produces the gammas under command from a surface computer system (e.g., computer system 312 in FIG. 3) and/or under command from a computer system within the tool (e.g., the computer system 410 in FIG. 4, as might be the case in the case of measuring-while-drilling (MWD), logging-while-drilling (LWD) or slickline tools). As for continuous sources, the gamma source 416 could be a radioisotope (e.g., CS-137).

Still referring to FIG. 4, and particularly to the far gamma detector 410 as illustrative of both gamma detectors, a gamma detector in accordance with at least some embodiments comprises an enclosure 418 (shown in cross-section), and within the enclosure 418 resides: a crystal 420 (e.g., sodium iodide scintillation crystal, bismuth germinate scintillation crystal); a photo multiplier tube 422 in operational relationship to the crystal 420; and a processor 424 coupled to the photomultiplier tube 422. As gammas are incident upon/within the crystal 420, the gammas interact with the crystal 420 and flashes of light are emitted. Each flash of light itself is indicative of an arrival of a gamma, and the intensity of light is indicative of the energy of the gamma. The output of the photomultiplier tube 422 is proportional to the intensity of the light associated with each gamma arrival. The processor 424 quantifies the output as gamma energy and relays the information to a surface computer system (e.g., computer system 312 in FIG. 3) and/or a computer system within the tool (e.g., the computer system 410 in FIG. 4, as might be the case in the case of measuring-while-drilling (MWD), logging-while-drilling (LWD) or slickline tools).

In operation of the tool 400, the gamma source 416 irradiates the formation with gammas such that a gamma flux is created around the tool 400 and extending into the surrounding formation 122. The gammas interact with elements that make up the minerals in the formation by way of a variety of mechanisms. In particular, after one or more collisions (and corresponding loss of energy) some of the gammas find their way to back to the gamma detectors 412 and 414. Other gammas, after one or more collisions (and corresponding loss of energy) are absorbed by atoms of the formation and/or formation evaluation tool 400.

The energy spectrum of the gammas created by the collisions with formation atoms and measured at each gamma detector is characteristic of a variety of parameters, such as standoff, density of the formation, photoelectric attenuation coefficient of the formation, photoelectric attenuation coefficient of the invaded fluid, porosity, and depth of invasion of the drilling fluid into formation. While the gammas measured at each gamma detector may be more sensitive to one parameter than to other parameters, in many cases some or all the parameters noted may affect the actual gamma count rates at each gamma detector.

Figure 5:
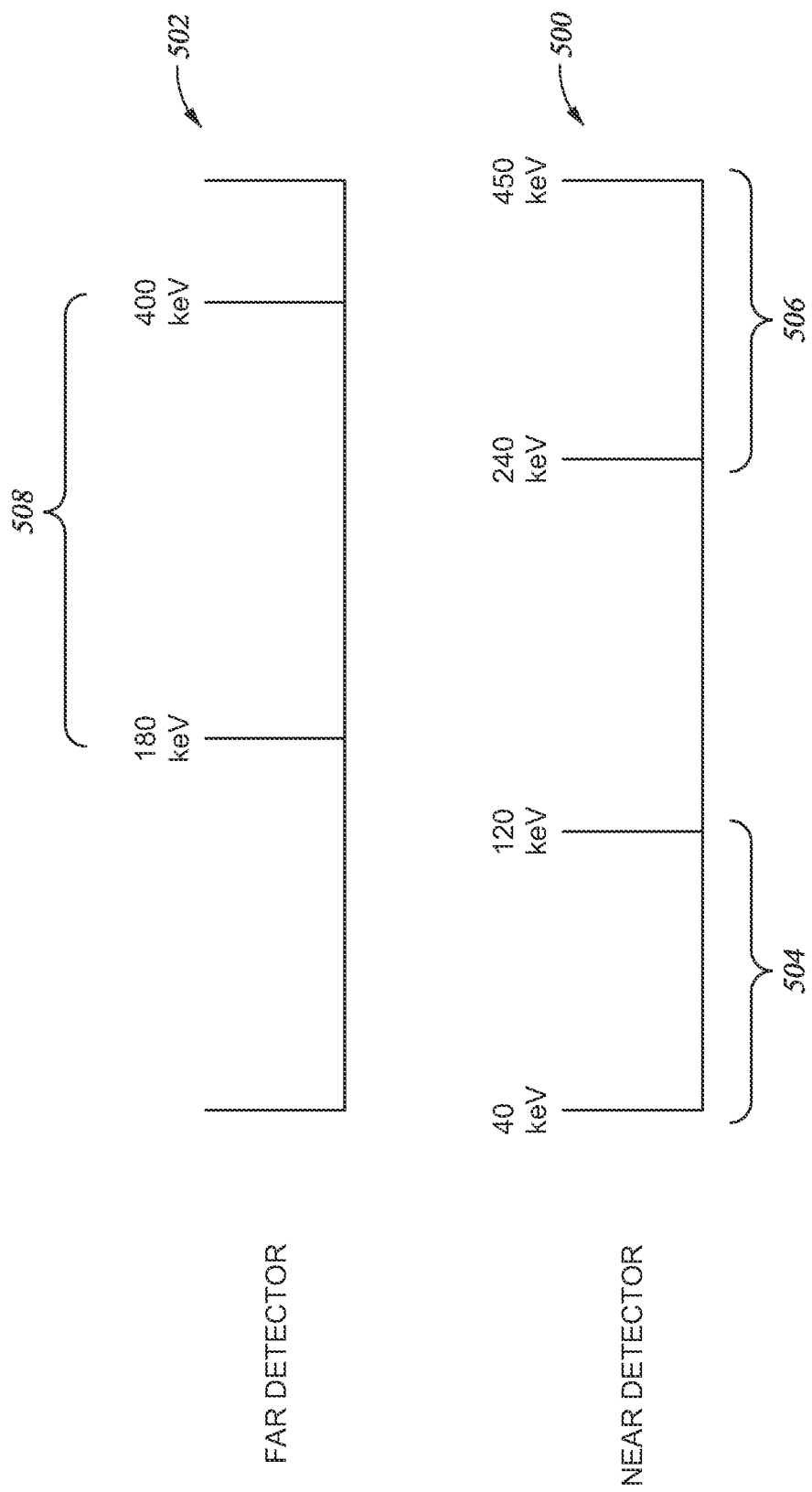
FIG. 5 graphically shows illustrative energy bins for the near and far gamma detectors, and in accordance with at least some embodiments.

In accordance with at least some embodiments, each gamma arrival at each gamma detector is tracked based on energy. More particularly, in some embodiments a gamma energy range of interest is broken into a plurality of energy channels or "bins". While possible to track the specific energy of each gamma arrival, in some embodiments the energy spectrum of interest is divided into bins, and a count or count rate of arrivals in each bin is used, rather than the specific energy of each arrival. FIG. 5 graphically illustrates the use of energy channels or bins. In particular, FIG. 5 shows a set of bins 500 for the near gamma detector 414, and a set of bins 502 for the far gamma detector 412. For each gamma arrival, the intensity of the light produced by the crystal in the detector is indicative of the energy of the gamma. Based on the energy, a count value in a bin is incremented. For example, when a gamma arrives at the near gamma detector 414 having energy in the range of about 40 keV to about 120 keV, the count value in the bin 504 is incremented. Likewise, when a gamma arrives at the near gamma detector 414 having energy in the range of about 240 keV to about 450 keV, the count value in the bin 506 is incremented. In some cases, there are gamma arrivals at the near gamma detector 414 with energies that are either not counted by the tool, or if they are counted by the tool the count values may not be used in determining the various parameters of interest. For example, gamma arrivals at the near gamma detector 414 having energies between about 120 keV and about 240 keV may not be counted or may be ignored.

Likewise, with respect to the far gamma detector 412, for each gamma arrival the intensity of the light produced by the crystal in the detector is indicative of the energy of the gamma. Based on the energy, a count value in a bin is incremented. For example, when a gamma arrives at the far gamma detector 412 having energy in the range of about 180 keV to about 400 keV, the count value in the bin 508 is incremented. In some cases, there are gamma arrivals at the far gamma detector 412 with energies that are either not counted by the tool, or if they are counted by the tool the count values may not be used in determining the various parameters of interest. For example, gamma arrivals at the far gamma detector 412 having energies outside the range of 180 keV and about 400 keV may not be counted or may be ignored. The specification now turns to a more thorough description of the problem associated with formate drilling fluids and measuring formation properties.

Traditional drilling fluids, as they reside within the borehole, may have relatively high density; however, the density of traditional drilling fluid is comprised of a base fluid (such as oil or water) and the presence of various heavy particles mixed with and suspended in solution. That is, traditional drilling fluid may comprise a water or saltwater base (with a density of 1.0 grams per cubic centimeter (g/cc) and about 1.1 g/cc, respectively) or an oil-base (with a density less than 1.0 g/cc), and also comprise various heavy particle additives (e.g., clay) to increase the density. With respect to invasion into the formation, as traditional drilling fluid starts to invade the formation the various heavy particles are "filtered" out by the formation at the borehole wall. The various heavy particles form a layer around the borehole wall, referred to in the industry as "mud cake." There are two consequences related to the creation of the mud cake. First, the mud cake tends to seal the formation against invasion by the drilling fluid, and thus to some extent invasion of the formation by the drilling fluid may be self-limiting for traditional drilling fluids. The second consequence, of greater importance with respect to the various embodiments, is that fluid that actually invades the formation has lower density than the drilling fluid as that fluid resides in the borehole because the heavy particles are filtered out. So, for example, for a traditional water-based drilling fluid having a density greater than 1.0 g/cc as that drilling fluid resides in the borehole, the density of the fluid that invades the formation will be about 1.0 g/cc, that of the water base. Because the density of the fluid that actually invades the formations is close to the density of the displaced hydrocarbons in the formation, in some cases invasion does not significantly affect measurements by nuclear formation evaluation tools.

Formate drilling fluids (e.g., cesium formate, potassium formate, and the like), by contrast, are inherently heavier than base fluids for traditional drilling fluid. For example, mixtures of potassium formate and cesium formate fluids that are used for heavy formate drilling fluids may have a density of 1.30 g/cc to 2.20 g/cc, and in some cases 1.57 g/cc to 2.20 g/cc, and also have higher photoelectric attenuation coefficients than traditional drilling base fluids. Because of the higher density than the base fluids for traditional drilling fluid, few or no additives to increase density may be used. Because of the lack of additives, or use of fewer additives, formate drilling fluid may tend to invade formations further because of the lack of, or a less thick, mud cake build up. Also, the density of the formate within the formation and the photoelectric attenuation coefficient adversely affect nuclear measurements of formation parameters, such as density and porosity. For example, if a virgin formation was oil filled, the density of the fluid within the formation may double because of formate invasion, which may adversely affect measurements of formation density.

As another example, consider photoelectric attenuation coefficient. Photoelectric attenuation coefficient, in the context of the various embodiments, is a value indicative of the likelihood that lower energy gammas will be absorbed by atoms of a substance. Most oilfield service companies do not directly refer to photoelectric attenuation coefficient, but instead refer to a value known as "Pe". For pure elements, Pe is calculated as:

$$Pe=(Z/10)^{3.6} \qquad (2)$$

where Z is the atomic number. For other mixed substances, technology exists to make Pe determinations (see, e.g., Gordon L. Moake, "Using Computer Modeling To Generate Accurate Pe Equations", SPWLA 52$^{nd}$ Annual Logging Symposium, May 14-18, 2011). Pe, however, is proportional to the ratio of the photoelectric absorption cross-section of the substance to the Compton cross-section for the substance. The balance of specification, and claims, will reference Pe rather than photoelectric attenuation coefficient. Most earth formations have a Pe of 5.1 or less prior to invasion; whereas, many formate drilling fluids have a Pe of 10 or higher. Thus, invasion by formate drilling fluids may adversely affect measurements of formation density for this reason as well.

At least some embodiments are directed to measuring at least one property of formation by a gamma-gamma formation evaluation tool when the formation has been invaded by a high density drilling fluid (e.g., a drilling fluid having a density 1.57 g/cc or greater) and/or a drilling fluid with high Pe (e.g., greater than 5.1, or 10 or greater), such as cesium formate. In particular, in at least some embodiments the density of the formation prior to invasion (i.e., the density of the virgin formation) is of primary interest, but other parameters may be of interest as well (e.g., the depth of invasion). However, in addition to the primary unknowns of density and depth of invasion, there are other unknowns as well, such as the standoff. The various embodiments use three or more measurements from two or more gamma detectors to solve for parameters of interest.

More particularly, in at least some embodiments, using one of the various gamma-gamma tools described above, the illustrative embodiments measure several values. For example, some embodiments measure gamma counts or gamma count rates at the near gamma detector, and from the measurement determine a shallow or near density value (e.g., based on count rates at the near gamma detector 414). Some embodiments measure gamma count or gamma count rates at the far gamma detector, and from the measurements determine a deep or far density value (e.g., based on count rates at the far gamma detector 412). Some embodiments determine a value indicative of Pe using various gamma count rates. In some cases, the value indicative of Pe is the ratio of two energy ranges at a single detector (e.g., ratio of the gamma rate of energy bin 506 to the gamma count rate of energy bin 504). From this point forward in the specification, the value indicative of Pe will be referred to as just Pe, with the understanding that the measured gamma counts or count rates are proportional to Pe, but that Pe itself may not be measured.

At the theoretical level, with three illustrative measured values (near density, far density, and Pe), one may solve for the three unknowns (formation porosity, standoff, depth of invasion). However, the solution is non-trivial. That is, each of the illustrative measurements (near density, far density, and Pe) may be sensitive to the unknowns in such a fashion that finding equations that adequately represent the measurements can be extremely difficult.

Solving for the unknowns in accordance with at least some embodiments involves creating, possibly in advance, a set of modeled tool responses based on a range of values. For the illustrative measurements of near density, far density, and Pe, the modeled tool responses may comprise: a near density relationship that relates measured near density to depth of invasion (e.g., 0 to 8 inches) for a plurality of porosities (e.g., 10 p.u., 25 p.u., and 40 p.u.) and a plurality of standoff values (e.g., 0 inches, 0.25 inches, and 0.5 inches); a far density relationship that relates measured far density to depth of invasion (e.g., 0 to 8 inches) for a plurality of porosities (e.g., 10 p.u., 25 p.u., and 40 p.u.) and a plurality of standoff values (e.g., 0 inches, 0.25 inches, and 0.5 inches); and a Pe relationship that relates Pe to depth of invasion (e.g., 0 to 8 inches) for a plurality of porosities (e.g., 10 p.u., 25 p.u., and 40 p.u.) and a plurality of standoff values (e.g., 0 inches, 0.25 inches, and 0.5 inches).

Figure 6:
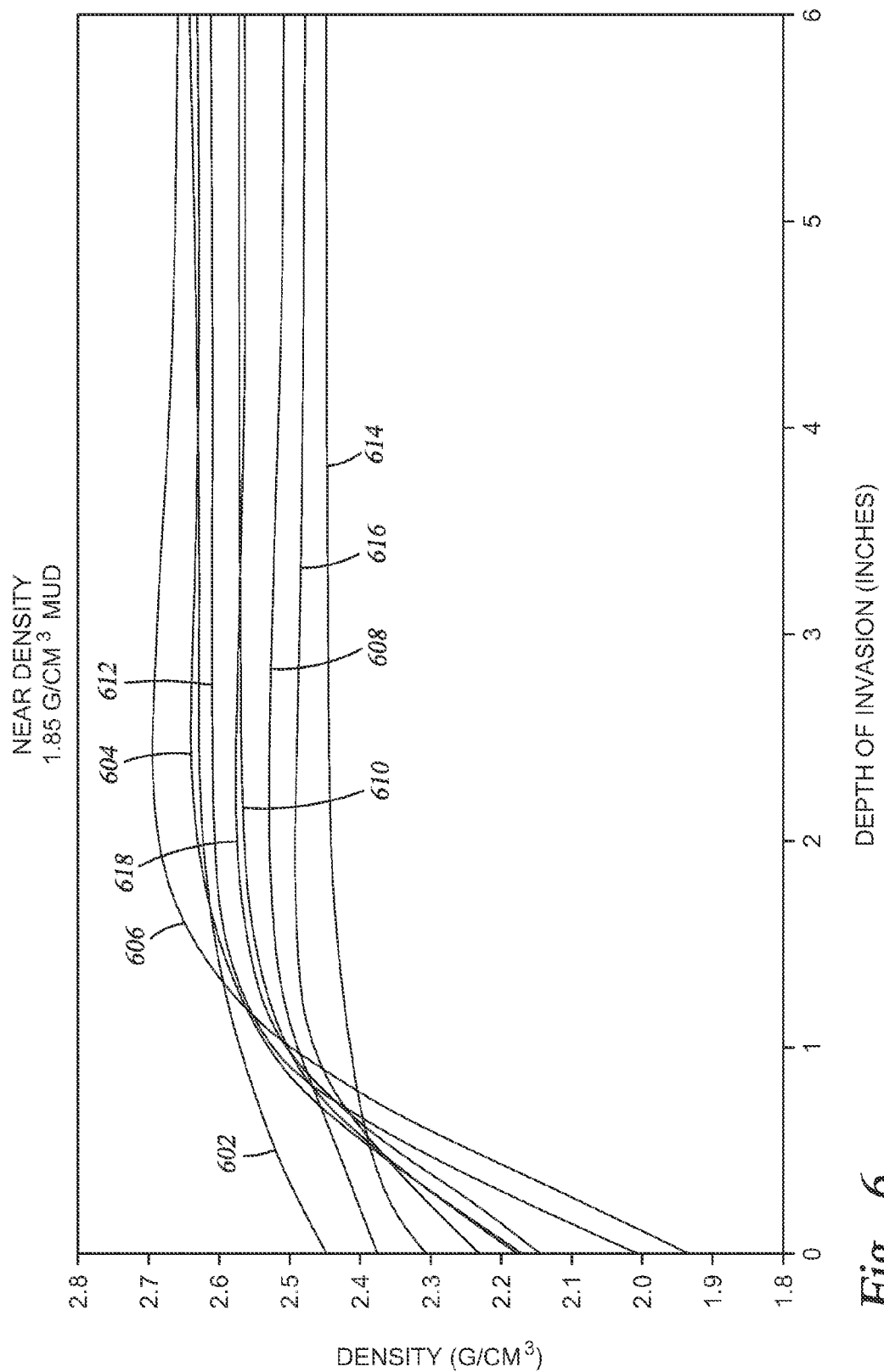
FIG. 6 shows a plot of modeled near density in accordance with at least some embodiments.

For example, FIG. 6 shows an illustrative graph relating near density to depth of invasion (for an assumed drilling fluid density of 1.85 g/cc). In particular, the illustrative graph plots a plurality of curves (each curve based on a different modeled porosity of the formation and modeled standoff of the tool) that show a modeled relationship between density and depth of invasion. In generating these curves, it was assumed that the formation rock matrix had the density of quartzite. The corresponding densities of other rock types can be easily computed from these curves. For example, for a modeled standoff of zero, line 602 shows the illustrative relationship based on an assumed porosity of the formation of 10 p.u., line 604 shows the illustrative relationship based on an assumed porosity of the formation of 25 p.u., and line 606 shows the illustrative relationship based on an assumed porosity of the formation of 40 p.u. For a modeled standoff of 0.25 inches, line 608 shows the illustrative relationship based on an assumed porosity of the formation of 10 p.u., line 610 shows the illustrative relationship based on an assumed porosity of the formation of 25 p.u., and line 612 shows the illustrative relationship based on an assumed porosity of the formation of 40 p.u. Finally, for a modeled standoff of 0.5 inches, line 614 shows the illustrative relationship based on an assumed porosity of the formation of 10 p.u., line 616 shows the illustrative relationship based on an assumed porosity of the formation of 25 p.u., and line 618 shows the illustrative relationship based on an assumed porosity of the formation of 40 p.u.

Figure 7:
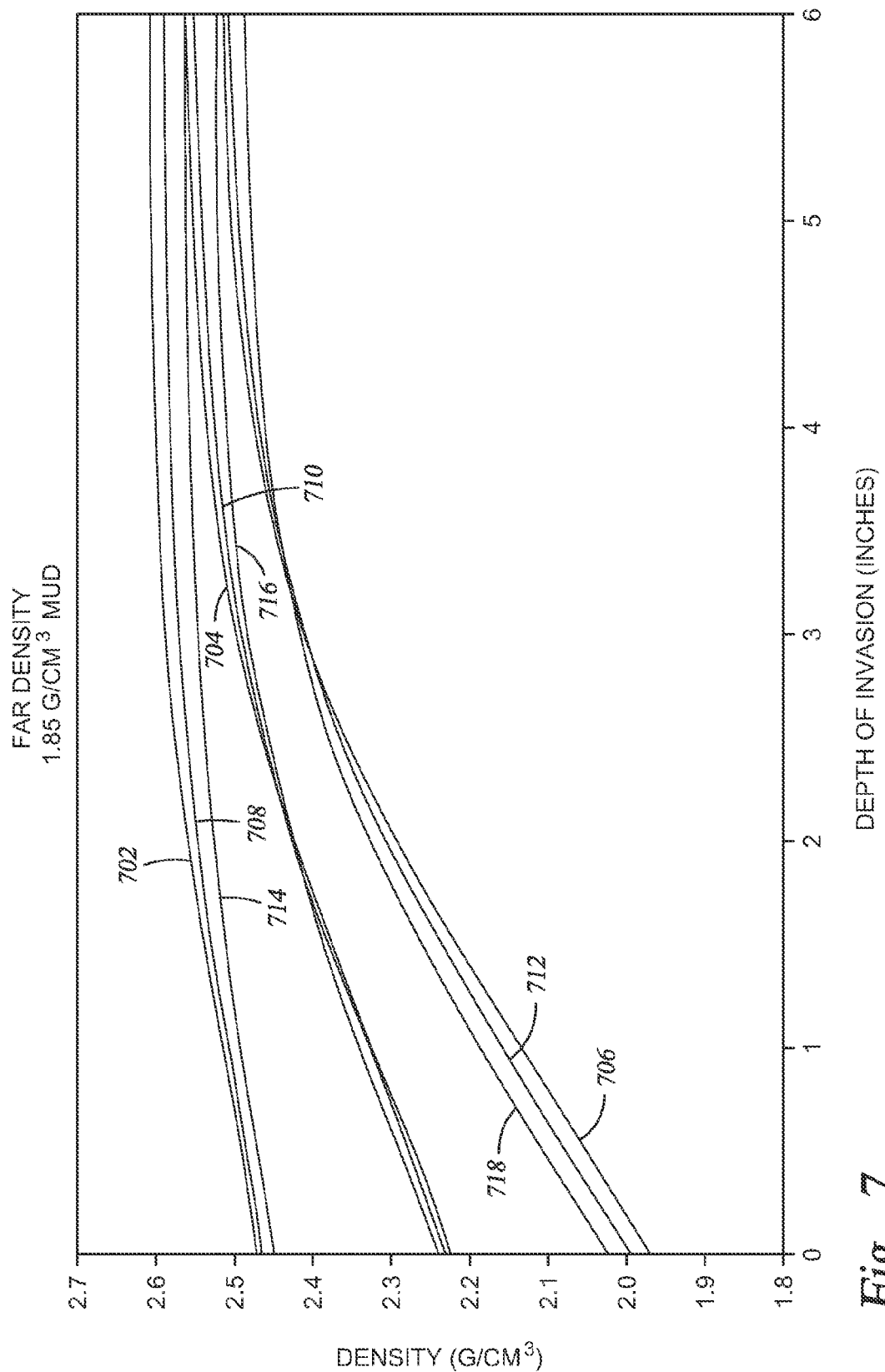
FIG. 7 shows a plot of modeled far density in accordance with at least some embodiments.

FIG. 7 shows an illustrative graph relating far density to depth of invasion (for an assumed drilling fluid density of 1.85 g/cc) for rock with a quartzite matrix. In particular, the illustrative graph plots a plurality of curves (each curve based a different modeled porosity of the formation and modeled standoff of the tool) that show a modeled relationship between density and depth of invasion. For example, for a modeled standoff of zero, line 702 shows the illustrative relationship based on an assumed porosity of the formation of 10 p.u., line 704 shows the illustrative relationship based on an assumed porosity of the formation of 25 p.u., and line 706 shows the illustrative relationship based on an assumed porosity of the formation of 40 p.u. For a modeled standoff of 0.25 inches, line 708 shows the illustrative relationship based on an assumed porosity of the formation of 10 p.u., line 710 shows the illustrative relationship based on an assumed porosity of the formation of 25 p.u., and line 712 shows the illustrative relationship based on an assumed porosity of the formation of 40 p.u. Finally, for a modeled standoff of 0.5 inches, line 714 shows the illustrative relationship based on an assumed porosity of the formation of 10 p.u., line 716 shows the illustrative relationship based on an assumed porosity of the formation of 25 p.u., and line 718 shows the illustrative relationship based on an assumed porosity of the formation of 40 p.u.

FIG. 8 shows an illustrative graph relating Pe to depth of invasion (for an assumed drilling fluid density of 1.85 g/cc) for rock with a quartzite matrix. In particular, the illustrative graph plots a plurality of curves (each curve based a different modeled porosity of the formation and modeled standoff of the tool) that show a modeled relationship between measured value of Pe and depth of invasion. For example, for a modeled standoff of zero, line 802 shows the illustrative relationship based on an assumed porosity of the formation of 10 p.u., line 804 shows the illustrative relationship based on an assumed porosity of the formation of 25 p.u., and line 806 shows the illustrative relationship based on an assumed porosity of the formation of 40 p.u. For a modeled standoff of 0.25 inches, line 808 shows the illustrative relationship based on an assumed porosity of the formation of 10 p.u., line 810 shows the illustrative relationship based on an assumed porosity of the formation of 25 p.u., and line 812 shows the illustrative relationship based on an assumed porosity of the formation of 40 p.u. Finally, for a modeled standoff of 0.5 inches, line 814 shows the illustrative relationship based on an assumed porosity of the formation of 10 p.u., line 816 shows the illustrative relationship based on an assumed porosity of the formation of 25 p.u., and line 818 shows the illustrative relationship based on an assumed porosity of the formation of 40 p.u.

The inventor of the present specification has determined that each curve of each of FIGS. 6, 7, and 8 may be mathematically represented by the following equation:

$$\text{Modeled\_Value} = \alpha(1 - e^{-ax}) + (b_0 + b_1 x + b_2 x^2)e^{-ax} \tag{2}$$

where Modeled_Value is a one of the curves of the figures (e.g., near density at 10 p.u. and zero standoff), x is the depth of invasion, and a, $\alpha$, $b_0$, $b_1$, and $b_2$ are free parameters determined (and most likely different) for each modeled value. Thus, the modeled tool responses may be represented mathematically, and the solution mechanism presented below may also be implemented mathematically, though the following example flow diagram will be explained in reference to illustrative FIGS. 6, 7, and 8 to help the reader visualize the process.

At a high level, finding a set of solutions can be thought of as testing possible solutions presented by the modeled responses by stepping through the modeled depths of invasion in predetermined increments. For each depth of invasion considered, a set of theoretical tool readings for several different porosities and several different tool standoffs are used to determine the best estimate of porosity and standoff, based upon the actual tool measurements. The theoretical tool readings for that porosity and standoff are then computed. A value indicative of the error or difference between the modeled values and the corresponding theoretical values is calculated. The set of values (depth of invasion, standoff, porosity) with most favorable error value (e.g., the lowest error) in some cases represents the selected solution. The density that would be measured in the absence of invasion can then be computed from assumed density of the rock matrix and density of the uninvaded formation fluid.

In some cases, finding a solution may involve testing a sufficient number of possible solutions with small enough invasion increments (e.g., hundredths of an inch) such that the solution with most favorable error value is the final answer after only one time through the process. However, the depth of invasion increments used for a "one time through" solution may be so small as to take significant computer processing time. The inventor of the present specification has found that, in some cases, finding a solution by working two or more times through the process may be faster, yet still arrive at an acceptable result. That is, the first time through the process a relatively large depth of invasion increment may be used (e.g., quarter inch). Assuming smaller error values represent answer closer to "correct", the first time through may locate a range of depths of invasion within which the global error minima may reside. Subsequent execution of the process can then be limited to a smaller range of depths of invasion, with smaller increments, until the actual global error minima is found.

Figure 9A:
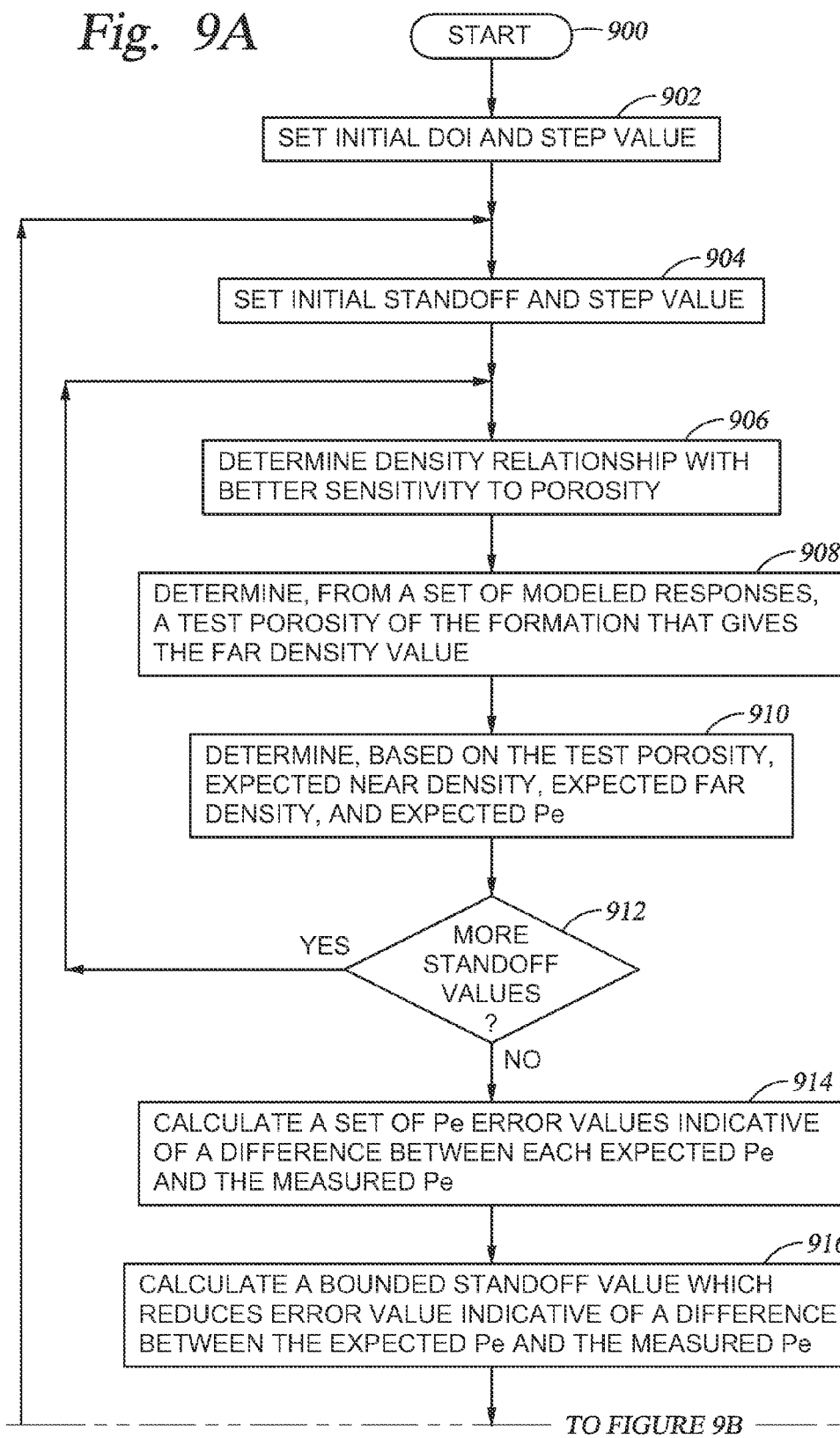
FIG. 9 (comprising FIGS. 9A and 9B) shows a method in accordance with at least some embodiments.

FIG. 9 (comprising FIGS. 9A and 9B) shows a method in accordance with at least some embodiments. In particular, FIG. 9 illustrates using the measured values, and the set of modeled responses, to solve for the various unknowns in accordance with at least some embodiments. The method starts (block 900) and proceeds to setting an initial test depth of invasion (DOI) (e.g., zero) as well step value to be used (e.g., 0.25 inch for depth of invasion) (block 902). Next, the illustrative method involves setting an initial test standoff (e.g., zero) as well as a step value to be used (e.g., 0.25 inch for standoff) (block 904).

Next, the illustrative method may involve determining a density relationship with better sensitivity to porosity (block 906). In the particular case illustrated by FIGS. 6, 7, and 8, the far density (FIG. 7) shows good sensitivity to porosity. In other situations, other modeled values (e.g., near density) may be chosen as the starting point for the calculations. So as not to unduly complicate the further discussion, it will be assumed that far density is selected; however, such shall not be read as a limitation, and where applicable other density readings may be initially selected.

From the illustrative modeled far density responses, a test porosity of the formation is selected that gives the measured far density value (block 908). For example, and referring briefly to FIG. 7, assuming a zero test depth of invasion and a measured far density value of 2.2 g/cc, the method may involve interpolating/extrapolating a test porosity from the known information. With the illustrative assumption, the test porosity resides between the 25 p.u. line 704 and the 40 p.u. line 706, and for purposes of this example, a test porosity of 30 p.u. may be determined. Again, while for purposes of explanation the specification refers to the illustrative graphs, in practice a computer system may perform the interpolation/extrapolation based on the equations that represent the data.

In some cases, the test porosity ultimately selected may be bounded. That is, because of factors such as standoff, density of the drilling fluid, and Pe of the drilling fluid, values of test porosity that are most directly indicated by the illustrative measured far density may be outside a predetermined range of expected or viable porosities for the known formation, and thus the test porosity may be limited to reside within a predetermined range of porosities different than a non-bounded interpolation/extrapolation would otherwise suggest.

Using the test porosity determined, the illustrative method may then determine an expected near density, an expected far density, and an expected Pe (block 910). That is, using the modeled responses and the test porosity determined, the method may involve interpolation/extrapolating between the modeled responses to calculate expected values for each parameter. In cases where the test porosity selected was not bounded or limited by a predetermined range, the expected far density will exactly match the measured far density. However, if the test porosity was limited in some fashion, in spite of illustratively starting with the measured far density as the mechanism to select the test porosity, the expected far density may differ from the measured far density.

The illustrative method then loops (block 912) for each standoff value. For the illustrative modeled responses represented by FIGS. 6, 7, and 8, the illustrative method may loop three times (e.g., for zero inch standoff, 0.25 inch standoff, and 0.5 inch standoff), each time calculating a test porosity and expected near density, expected far density, and expected Pe. Thus, a set of test porosities may be determined, along with a corresponding set of expected values.

Thereafter, the illustrative method involves, for each expected Pe, calculating an error value based on the difference between each expected Pe (that is, an expected Pe for each standoff value) and the measured Pe (block 914). The illustrative method then calculates a bounded standoff value which gives the most favorable an error value regarding expected and measured Pe (block 916). That is to say, from the illustrative three times through the upper loop of the method, three error values regarding Pe are determined. From the three illustrative error values, a bounded standoff value is interpolated/extrapolated that gives the most favorable (e.g., the lowest) error value. The bounded standoff value determined is referred as bounded because solutions that may give the most favorable error values, but which are not physically possible (e.g., negative standoff values), are excluded. Thus, while a bounded standoff values that provides a zero or near zero error may be possible in some situations, in other situations the selected standoff value will have a non-zero error.

Using the bounded standoff value determined (in block 916), the illustrative method may then determine an expected near density, an expected far density, and an expected Pe (block 918). That is, using the modeled responses and the bounded standoff value (for the test DOI), the method may involve interpolation/extrapolating between the modeled responses to calculate expected values for each parameter. Next, using expected values determined (in block 918), an overall error value is calculated indicative of near density error, far density error, and Pe error (block 920). With respect to the overall error calculation, in some cases the illustrative method involves calculating a "chi-squared" error, such as by application of the following equation:

$$\text{Error\_Value} = \sqrt{(\text{far\_density\_error})^2 + (\text{near\_density\_error})^2 + (\text{Pe\_error})^2} \quad (3)$$

where Error_Value is the error, far_density_error is the difference between the expected far density and the measured far density, near_density_error is the difference between the expected near density and the measured near density, and Pe_error is the difference between the expected Pe and the measured Pe. Other systems to calculate an overall error may be equivalently used.

Once an overall error value for the test depth of invasion and range of standoffs is determined, the value is saved, and the method moves to repeating the various steps for the next text depth of invasion (block 922). In some cases, the increment for depth of invasion is 0.25 inches, thus to test up to six inches invasion there may be 24 overall error values calculated and stored. Of course, smaller increments for depths of invasion, and deeper or shallower final depths of invasion may be used.

In some cases, a set of solutions indicated by the most favorable overall error may represent the final answer, particularly in cases where a significant number of depths of invasion are tested (i.e., small increment on the depth of invasion). However, in other cases the overall error values help narrow the search for the globally smallest overall error value, and thus set a range for performing again the illustrative method discussed to this point. To that end then, in accordance with at least some embodiments, the illustrative method involves selecting the smallest error value from the overall error values (block 924), and selecting the smallest abutting error value (i.e., the smaller of the nearest-neighbor error value) from the set of overall error values (block 926). That is, the smallest overall error value represents a depth of invasion, and the nearest-neighbor smallest overall error value represents a depth of invasion, and from the two depths of invasion a refined depth of invasion (i.e., slightly closer to the actual depth of invasion) is calculated (block 928). In some cases, the refined depth of invasion may be the average of (i.e., resides midway between) the depths of invasion implied by the two smallest error values. In other cases, the refined depth of invasion may be based on other factors, such as the absolute values of the error values. For example, if the absolute value of the error value of the nearest-neighbor is significantly different, such may imply that the final solution resides closer to the depth of invasion associated with the smallest error value.

Assuming the difference between the depth of invasion associated with the selected error value and the depth of invasion associated with the nearest-neighbor error value are above a predetermined threshold (block 930) (that is, the final solution not yet found), the various method steps are repeated for multiple standoffs, but for only one test depth of invasion at a time (i.e., the refined depth of invasion) (block 932). Once the illustrative method returns to block 924, there is an additional overall error value, and again the smallest error value is selected (block 924) and the smallest abutting error value is selected and the refined depth of invasion calculated (block 926).

The process of refinement repeats until the difference between the depth of invasion associated with the selected error value and the depth of invasion associated with the nearest-neighbor error value is below a predetermined threshold (e.g., less than 6 thousandths of an inch) (again block 930). If the difference is the below the threshold, an acceptable solution in the refinement has been found, and thus the method proceeds to convert the porosity determined using the matrix density and the fluid density of the uninvaded formation (block 934), output value indicative of density and/or a radial depth of invasion of the drilling fluid into the formation (block 936). Thereafter, the method ends (block 938).

So as not to unduly complicate the discussion, the formation evaluation tools are described to measure two density values and a value indicative of Pe. However, different measured values, including more measured values, may be equivalently used. For example, three measured values associated with three gamma detectors, and where at least two span different energy ranges (and are thus sensitive to Pe), may be used. Further still, with an additional measurement, and additional unknown may be solved for. For example, with an additional density measurement from a third gamma detector, the various embodiments may be adjusted to also solve for an unknown density of the drilling fluid.

Figure 10:
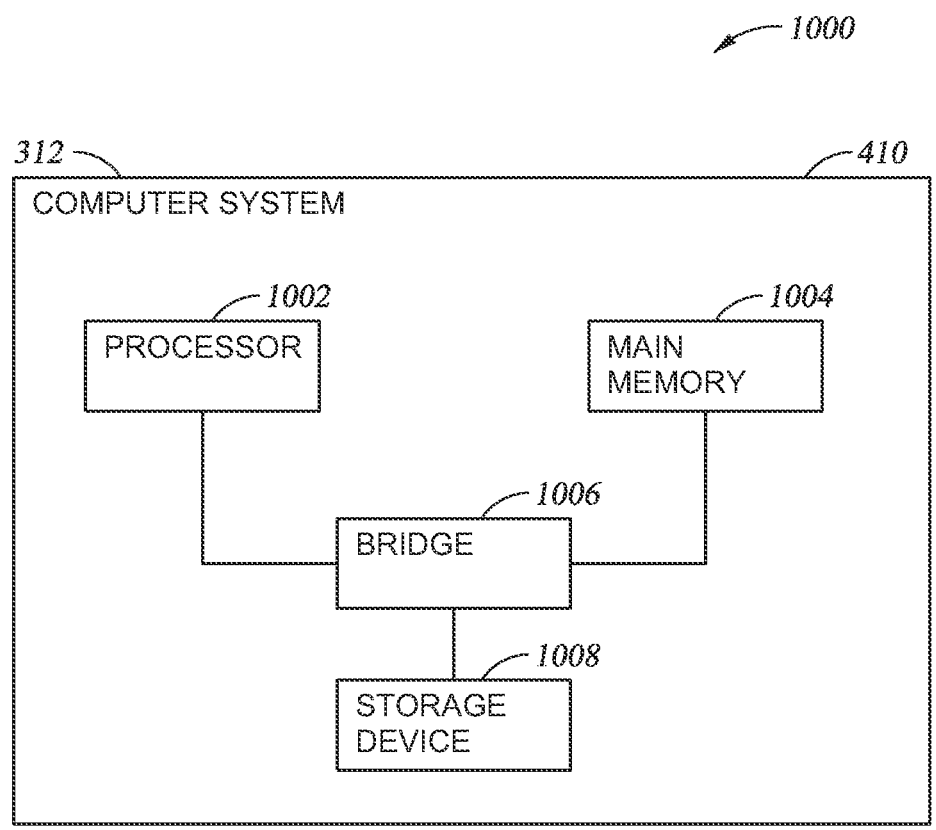
FIG. 10 shows a computer system in accordance with at least some embodiments.

FIG. 10 shows a computer system 1000, which is illustrative of a computer system upon which the various embodiments may be practiced. The computer system 1000 may be, for example, surface computer system 312, or the computer system 1000 may reside within the pressure vessel for MWD and LWD applications, for example computer system 410. The computer system 1000 comprises a processor 1002, and the processor couples to a main memory 1004 by way of a bridge device 1006. Moreover, the processor 1002 may couple to a long term storage device 1008 (e.g., a hard drive, "floppy" disk, memory stick, optical disc) by way of the bridge device 1006. Programs executable by the processor 1002 may be stored on the storage device 1008, and accessed when needed by the processor 1002. The program stored on the storage device 1008 may comprise programs to implement the various embodiments of the present specification, such as programs to solve for density of formation prior to invasion by the drilling and/or radial depth of invasion of the drilling fluid. In some cases, the programs are copied from the storage device 1008 to the main memory 1004, and the programs are executed from the main memory 1004. Thus, both the main memory 1004 and storage device 1008 shall be considered computer-readable storage mediums. The results of the method calculated by the computer system 1000 may be sent to a display device which may make a representation for viewing.

From the description provided herein, those skilled in the art are readily able to combine software created as described with appropriate general-purpose or special-purpose computer hardware to create a computer system and/or computer sub-components in accordance with the various embodiments, to create a computer system and/or computer sub-components for carrying out the methods of the various embodiments and/or to create a non-transitory computer-readable medium (i.e., not a carrier wave) that stores a software program to implement the method aspects of the various embodiments.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed:

1. A method comprising:
   placing a tool within a borehole, the borehole penetrating a formation and the borehole comprising drilling fluid;
   irradiating the formation with gammas from a source of gammas that resides within the tool, wherein drilling fluid has invaded the formation, and wherein Pe of the drilling fluid that has invaded the formation is greater than Pe of the formation;
   determining a first value indicative of a parameter of the formation, the first value based on a first set of gammas detected at a first gamma detector;
   determining a second value indicative of a parameter of the formation, the second value based on a second set of gammas detected at a second gamma detector;
   determining a third value, the third value determined based on gammas in an energy range different than used in determining the first value; and
   calculating, using the first, second, and third values, at least one selected from the group consisting of: a standoff; a formation porosity; a formation density prior to invasion by the drilling fluid; and radial depth of invasion of the drilling fluid into the formation.

2. The method of claim 1 wherein Pe of the drilling fluid is greater than 5.1.

3. The method of claim 1 wherein Pe of the drilling fluid is 10.0 or greater.

4. The method of claim 1:
   wherein determining the first value further comprises determining the first value being a value indicative of density of the formation; and
   wherein determining the second value further comprises determining the second value being a value indicative of density of the formation.

5. The method of claim 1 wherein determining a third value further comprises determining a value indicative of Pe of the formation.

6. The method of claim 5 wherein determining a value indicative of Pe of the formation further comprises taking a ratio of a first count rate of gammas in a first range of energies and a second count rate of gammas in a second range of energies.

7. The method of claim 1 wherein calculating further comprises:
   finding a set of solutions using a set of modeled responses for an assumed depth of invasion;
   calculating an error value from the solutions;
   re-performing, for a plurality of assumed depths of invasion, the finding and the calculating, the re-performing creates a plurality of error values; and
   selecting a set of solutions based on the plurality of error values.

8. The method of claim 1 wherein calculating further comprises:
   a) determining, from a set of modeled responses, a test porosity of the portion of the formation that gives the first value, the determining the test porosity based on an assumed standoff and an assumed depth of invasion;
   b) determining, from the set of modeled responses, an expected second value based on the test porosity;
   c) determining, from the set of modeled responses, an expected third value based on the test porosity;
   d) calculating a value indicative of a difference between the third value and the expected third value;
   e) repeating, for plurality of standoffs, steps a), b), c), and d);
   f) re-performing, for a plurality of assumed depths of invasion, steps a), b), c), d), and e); and
   g) selecting a set of solutions based on the values indicative of the difference.

9. The method of claim 1 wherein irradiating the portion of the formation with gammas further comprises irradiating with gammas having energy of over 600 kilo electron Volts (keV).

10. The method of claim 1 wherein placing the tool further comprises at least one selected from the group consisting of: suspending a logging tool by a wireline; and placing the tool within a drill string having a drill bit on a distal end of the drill string.

11. A system comprising:
    a formation evaluation tool comprising:
      a tool body;
      a source of gammas disposed within the tool body;
      a first gamma detector disposed within the tool body at a first longitudinal distance from the source of gammas; and
      a second gamma detector disposed within the tool body at a second longitudinal distance from the source of gammas;
    a processor operatively coupled to the gamma detectors;

a memory coupled to the processor, the memory storing a program that, when executed by the processor, causes the processor to:

count gamma arrivals at the first gamma detector, the counting as a function of energy, and the counting creates a first set of gammas;

count gamma arrivals at the second gamma detector, the counting as a function of energy, and the counting creates a second set of gammas;

determine a first value indicative of a parameter of the formation, the first value based on the first set of gammas;

determine a second value indicative of a parameter of the formation, the second value based on the second set of gammas;

determine a third value, the third value determined based on gammas in an energy range different than used in determining the first value; and calculate, using the first, second, and third values, at least one selected from the group consisting of: a standoff; a formation porosity; a formation density prior to invasion by the drilling fluid; and radial depth of invasion of the drilling fluid into the formation.

12. The system of claim 11 wherein when the processor calculates, the program causes the processor to at least one selected from the group consisting of: calculate correcting for drilling fluid in the formation having a Pe greater than 5.1; and calculate correcting for drilling fluid in the formation having a Pe greater than 10.

13. The system of claim 11 wherein when the processor calculates, the program further causes the processor to:
finding a set of solutions using a set of modeled responses for an assumed depth of invasion;
calculating an error value from the solutions;
re-performing, for a plurality of assumed depths of invasion, the finding and the calculating, the re-performing creates a plurality of error values; and
selecting a set of solutions based on the plurality of error values.

14. The system of claim 11 wherein when the processor determines the second value, the program further causes the processor to take a ratio of a first count rate of gammas in a first range of energies energy and a second count rate of gammas in a second range of energies, the second range of energies different than the first range of energies.

15. The system of claim 11 wherein the tool body is at least one selected from the group consisting of: a logging-while-drilling tool; and a wireline logging tool.

16. A non-transitory computer-readable medium storing a program that, when executed by a processor, causes the processor to:
determine a first value indicative of a parameter of a formation, the first value based on a first set of gammas detected at a first gamma detector;
determine a second value indicative of a parameter of the formation, the second value based on a second set of gammas detected at a second gamma detector;
determine a third value, the third value determined based on gammas in an energy range different than used in determining the first value; and
calculate, using the first, second, and third values, at least one selected from the group consisting of: a standoff; a formation porosity; a formation density prior to invasion by the drilling fluid; and radial depth of invasion of the drilling fluid into the formation.

17. The non-transitory computer-readable medium of claim 16 wherein when the processor calculates, the program causes the processor to at least one selected from the group consisting of: calculate correcting for drilling fluid in the formation having a Pe greater than 5.1; and calculate correcting for drilling fluid in the formation having a Pe greater than 10.

18. The non-transitory computer-readable medium of claim 16 wherein when the processor determines the third value, the program further causes the processor to take a ratio of a first count rate of gammas in a first range of energies energy and a second count rate of gammas in a second range of energies, the second range of energies different than the first range of energies.

19. The non-transitory computer-readable medium of claim 16 wherein when the processor calculates, the program further causes the processor to:
a) find a set of solutions using a set of modeled responses for an assumed depth of invasion;
b) calculate an error value from the solutions;
c) re-perform, for a plurality of assumed depths of invasion, steps a) and b), the re-performing creates a plurality of error values; and
d) selecting a set of solutions based on the plurality of error values.

20. The non-transitory computer-readable medium of claim 16 wherein when the processor calculates, the program further causes the processor to:
a) determine, from a set of modeled responses, a test porosity of the portion of the formation that gives the first value, the determining the test porosity based on an assumed standoff and an assumed depth of invasion;
b) determine, from the set of modeled responses, an expected second value based on the test porosity;
c) determine, from the set of modeled responses, an expected third value based on the test porosity;
d) calculate a value indicative of a difference between the third value and the expected third value;
e) repeat steps a), b), c), and d) for plurality of standoffs; and
f) repeat steps a), b), c), d) and e) for a plurality of assumed depths of invasion; and
g) select a set of solutions based on the values indicative of the difference.

* * * * *